US007337066B2

(12) United States Patent
Neiss (10) Patent No.: US 7,337,066 B2
(45) Date of Patent: Feb. 26, 2008

(54) SYSTEM AND METHOD FOR AUTOMATED BASELINE CORRECTION FOR RAMAN SPECTRA

(75) Inventor: Jason H. Neiss, Pittsburgh, PA (US)

(73) Assignee: ChemImage, Corporation, Pittsburgh, PA (US)

( * ) Notice: Subject to any disclaimer, the term of this patent is extended or adjusted under 35 U.S.C. 154(b) by 0 days.

(21) Appl. No.: 11/635,659

(22) Filed: Dec. 8, 2006

(65) Prior Publication Data

US 2007/0136014 A1 Jun. 14, 2007

Related U.S. Application Data

(60) Provisional application No. 60/748,194, filed on Dec. 8, 2005.

(51) Int. Cl.
*G06F 19/00* (2006.01)
(52) U.S. Cl. ............................ 702/8; 702/124; 702/189
(58) Field of Classification Search .................... 702/8, 702/66, 71, 86, 106, 124, 189; 398/79; 327/98; 372/3; 359/327, 334; 307/401
See application file for complete search history.

(56) References Cited

U.S. PATENT DOCUMENTS

| 4,616,898 | A  | * | 10/1986 | Hicks, Jr. ................... 385/24 |
| 6,281,971 | B1 | * | 8/2001  | Allen et al. ................. 356/301 |
| 6,763,322 | B2 | * | 7/2004  | Potyrailo et al. ........... 702/189 |
| 2003/0191398 | A1 | * | 10/2003 | Motz et al. ................. 600/478 |
| 2004/0019283 | A1 | * | 1/2004  | Lambert et al. ............ 600/476 |

OTHER PUBLICATIONS

Creely et al., 'Dual Wavelenght Optical Tweezers for Confocal RAman Spectroscopy', 2004, Optics Communication Publication, vol. 245, pp. 465-470.*
Zhengmao, IEEE Article, 'Principal Component Analysis Approach for Biomedical Sample Identification', 2004, IEEE Publication, pp. 1348-1353.*
Williams, Antony, Golotvin, Sergey, Vodopianov, Eugene, Shockcor, John, "The ABC of Metabonomics Automated Baseline Correction,".
Mazet, Vincent, et al., "Background Removal from Spectra by Designing and Minimising a Non-Quadratic Cost Function," Elsevier, 2004, p. 121-133.
Golotvin, Sergey and Williams, Antony, "Improved Baseline Recognition and Modeling of FT NMR Spectra," Advanced Chemistry Development, p. 1-8.
Schulze, G., et al., "Investigation of Selected Baseline Removal Techniques as Candidaates for Automated Implementation," Applied Spectroscopy, 2005, V. 59, No. 5, p. 545-574.

* cited by examiner

*Primary Examiner*—Eliseo Ramos-Feliciano
*Assistant Examiner*—Elias Desta
(74) *Attorney, Agent, or Firm*—Duane Morris, LLP (57) ABSTRACT

A system and method for automated baseline correction for Raman spectra is disclosed which may operate as a piecewise-linear baseline correction function. In an embodiment, a first set of data points from a Raman spectrum are determined to be baseline data points, a second set of data points from the Raman spectrum are determined to be baseline data points where the second set of data points are not contiguous with the first set of data points. The gap between the first and second set of data points is bridged by a straight line thereby forming an estimated baseline. The estimated baseline is smoothed and then subtracted from the Raman spectrum resulting in an adjusted-baseline Raman spectrum.

31 Claims, 7 Drawing Sheets

SYSTEM AND METHOD FOR AUTOMATED BASELINE CORRECTION FOR RAMAN SPECTRA

RELATED APPLICATIONS

The present application hereby incorporates by reference in its entirety and claims priority benefit from U.S. Provisional Patent Application Ser. No. 60/748,194 filed 8 Dec. 2005 titled "System and Method for Automated Baseline Correction for Raman Spectra".

BACKGROUND

Raman spectra may be obtained from a variety of samples and are extremely useful in helping to characterize the materials that make up the sample. Raman spectra are derived from a material's intrinsic vibrational spectroscopic signature, which is highly sensitive to the composition and structure of the material and its local chemical environment. Raman spectra and Raman images may be obtained with little or no sample preparation and are widely applicable for materials research, failure analysis, process monitoring, clinical diagnostics, forensic analysis, medical research, etc.

Raman spectra may be obtained in a number of ways, as is known in the art. As a non-limiting example, a laser photon source may be used to illuminate the sample. Photons that may be reflected, emitted, and/or scattered by the sample are collected and passed through an electronically-tunable filter, such as a liquid crystal tunable filter ("LCTF"), and acousto-optic tunable filter ("AOTF") or other similar filters known in the art. The filtered photons may be detected by a photon detection device, such as a charge-coupled device ("CCD"). The output of the CCD may be used to form a Raman spectrum of the sample. One problem with the obtained Raman spectrum is due to fluorescence of the sample. When the sample fluoresces, the fluorescing photons may be detected by the photon detector thereby distorting the Raman spectrum obtained from the sample. This distortion may have a number of effects, one of interest is a change in the baseline of the Raman spectrum. This change may typically be seen as an elevation of the intensity of baseline data points in the Raman spectrum. This elevation of intensity may tend to obscure the peaks of the Raman spectrum thereby making it difficult for a technician or operator to obtain a correct analysis of the sample.

There exists in the art a number of methodologies for correcting the baseline of spectra. One in particular is a paper entitled "The ABC of Metabonomics Automated Baseline Correction" by Antony Williams, Sergey Golotvin, Eugene Vodopianov, and John Shockcor (the "ABC Paper"). The paper was presented during the $42^{nd}$ ENC meeting in Orlando, Fla., USA between 11-16 Mar. 2001, and is incorporated herein by reference in its entirety. The paper discloses, in part, a method for baseline correction for nuclear magnetic resonance ("NMR") spectra comprising two basic steps: baseline recognition and baseline modeling.

The baseline recognition procedure divides the points in the NMR spectrum into either "baseline" points or "peak" points. This is performed by using a sliding window centered on a particular data point. A maximum and a minimum value for the points in the window are obtained and the difference is compared with a minimal standard deviation value. The minimal standard deviation value is obtained by dividing the NMR spectrum into 32 regions and, for each of the 32 regions, calculating the standard deviation of the points in the region. The minimal standard deviation value is used for comparison with each of the sliding window difference values obtained. The baseline points will typically be separated into groups with a gap between the groups where the "peak" points are located.

In the baseline modeling procedure, the gaps between the groups of baseline points are connected with a straight line segment rather than using a polynomial fit. The resulting spectrum is then smoothed and subtracted from the NMR spectrum. The result is a baseline-corrected NMR spectrum.

While the procedure disclosed in the ABC Paper apparently works well with NMR spectra, it does not adapt very well to Raman spectra. Therefore, a need exists to apply an automated baseline correction procedure, and apparatus therefor, to Raman spectra to correct for, among other things, fluorescence effects in the Raman spectra.

Accordingly, it is an object of the present disclosure to apply a system and/or method for automated baseline correction to Raman spectra. The method and/or apparatus may be employed to correct a Raman spectrum baseline that is corrupted by, for example, fluorescence from the sample from which the Raman spectrum is obtained. In an embodiment, a first set of data points from a Raman spectrum are determined to be baseline data points and a second set of data points from the Raman spectrum are determined to be baseline data points where the second set of data points are not contiguous with the first set of data points. The gap between the first and second set of data points may be bridged by a straight line thereby forming an estimated baseline. The estimated baseline may be smoothed and then subtracted from the Raman spectrum resulting in an adjusted-baseline Raman spectrum.

In another embodiment, the determination of baseline data points includes determining a first quantity as a function of a maximum and a minimum of a value for data points in a first group of data points; determining a second quantity as a function of a signal to noise ratio of the Raman spectrum and as a function of a weighted standard deviation for the value of the data points in a second group of data points; and for ones of the data points, comparing the first quantity to the second quantity to thereby determine a first set of data points to be baseline data points.

In yet another embodiment, the determination of baseline data points includes determining the second quantity above which includes dividing the Raman spectrum into a predetermined number of sections; determining, for each section of the predetermined number of sections, a standard deviation for the value of the data points in each section; determining a weighted standard deviation from the determined standard deviation for each section of the predetermined number of sections; and multiplying the weighted standard deviation by a predetermined amount wherein the predetermined amount is a function of a signal to noise ratio of the Raman spectrum.

In still another embodiment, an apparatus for adjusting a baseline for a Raman spectrum includes means for providing a Raman spectrum with plural data points each of which has a value (such as an intensity value); first circuitry for determining a first and a second set of data points to be baseline data points where the first and second sets of data points are not contiguous; second circuitry for bridging the gap between the first and second sets of data points to thereby form an estimated baseline; filtering circuitry for smoothing the estimated baseline; and signal processing circuitry for subtracting the smoothed estimated baseline from the Raman spectrum.

In a further embodiment, a system for adjusting a baseline for a Raman spectrum including means for providing a Raman spectrum with plural data points each of which has a value (such as an intensity value); and a processor programmed to perform a plurality of executable instructions, the instructions comprising: determining a first and a second set of data points to be baseline data points where the first and second set of data points are not contiguous; bridging the gap between the first and second sets of data points to thereby form an estimated baseline; smoothing the estimated baseline; and for subtracting the smoothed estimated baseline from the Raman spectrum.

In yet a further embodiment, the above processor is programmed to perform further executable instructions, the further instructions comprising: determining the baseline data points by determining a first quantity as a function of a maximum and a minimum of a value for data points in a first group of data points; determining a second quantity as a function of a signal to noise ratio of the Raman spectrum and as a function of a weighted standard deviation for the value of the data points in a second group of data points; and for ones of the data points, comparing the first quantity to the second quantity to thereby determine a first set of data points to be baseline data points.

In still a further embodiment, the above processor is programmed to perform still further executable instructions, the still further instructions comprising: determining the second quantity by dividing the Raman spectrum into a predetermined number of sections; determining, for each section of the predetermined number of sections, a standard deviation for the value of the data points in each section; determining a weighted standard deviation from the determined standard deviation for each section of the predetermined number of sections; and multiplying the weighted standard deviation by a predetermined amount wherein the predetermined amount is a function of a signal to noise ratio of the Raman spectrum.

DETAILED DESCRIPTION

A system and method for automated baseline correction for Raman spectra is disclosed which may operate as a piecewise-linear baseline correction function. In an embodiment, a first set of data points from a Raman spectrum are determined to be baseline data points, a second set of data points from the Raman spectrum are determined to be baseline data points where the second set of data points are not contiguous with the first set of data points. The gap between the first and second set of data points is bridged by a straight line thereby forming an estimated baseline. The estimated baseline is smoothed and then subtracted from the Raman spectrum resulting in an adjusted-baseline Raman.

As discussed above, the prior art includes many methodologies and schemes for correcting the baseline of a spectrum, including the methodology discussed in the ABC Paper. However, there are a number of significant variations required in applying the prior art baseline correction methodology in the ABC Paper to Raman spectra due, at least in part, to the unique character of Raman spectra. As a non-limiting example, some Raman peaks are quite small, i.e., the intensity value for the data points that are part of the peak may not be much greater than the intensity value for the noise. Therefore, the application of the prior art baseline correction methodology must be modified to take into account this feature of Raman spectra. Consequently, the use of the minimum value of the standard deviations for the separate sections into which the Raman spectrum is divided will result in the loss of important Raman data. The inventor has discovered that taking a weighted average standard deviation of the standard deviation values for the separate sections overcomes this deficiency in the prior art. Furthermore, the quantity by which the weighted standard deviation is multiplied must be adjusted as a function of the signal-to-noise ratio ("SNR") of the Raman spectrum. In cases where the SNR is low, a smaller value for n (see equation (2), below) must be used in order to effectively differentiate a "peak" data point (i.e., a data point that is representative of a Raman signal) from a baseline data point (i.e., a data point that is representative of noise). In the case where the SNR is high, the value to be used for n may be larger since there exists sufficient differentiation between Raman signal data points and noise data points.

An additional fundamental difference between a Raman spectrum and, for example, the NMR spectrum in the ABC Paper is that there may be prior knowledge of where a Raman signal should appear in a Raman spectrum depending on, for example, the wavelength of the illuminating light. Using this knowledge advantageously allows for limiting the baseline correction algorithm to only those areas of the Raman spectrum where a Raman signal should appear. This effectively eliminates errors from spurious data points in portions of the Raman spectrum where no Raman signal may appear (i.e., those places of the Raman spectrum that are expected to contain nothing but noise).

Figure 1:
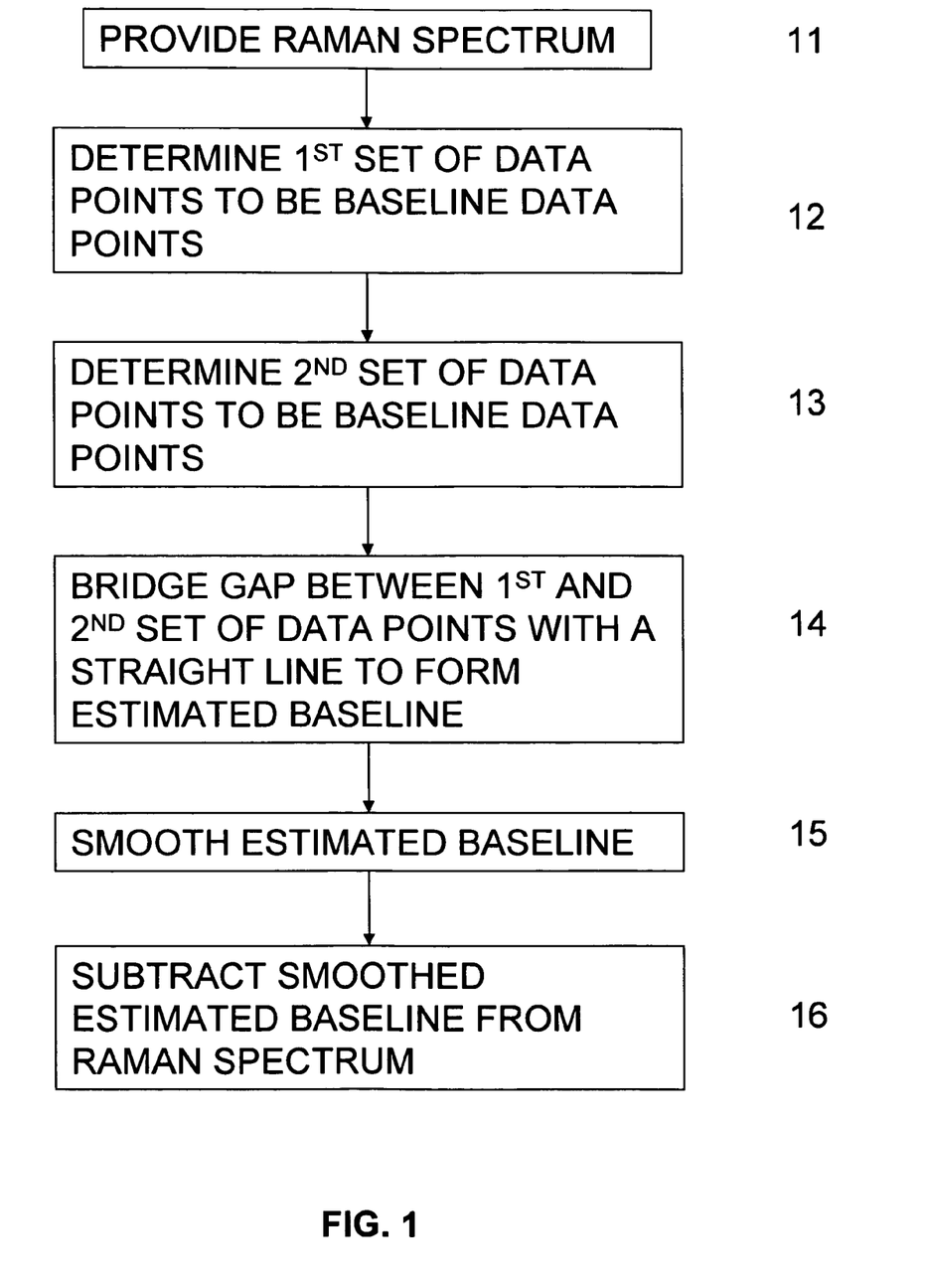
FIG. 1 is a flow chart illustrating procedural steps for adjusting a baseline for a Raman spectrum according to an embodiment of the disclosure.

With attention directed toward FIG. 1, a flow chart illustrating procedural steps for adjusting a baseline for a Raman spectrum according to an embodiment of the disclosure. At block 11, a Raman spectrum is provided. The Raman spectrum may contain multiple data points, some of which are indicative of Raman scattering and therefore represent a Raman signal (i.e., "peak" data points). Other data points are simply noise. As discussed above, the application of an automated baseline correction such as described herein to a Raman spectrum is novel. At block 12, a determination is made regarding some of the Raman spectrum data points so that some of the Raman spectrum data points are classified as baseline (i.e., noise) data points. A first set of the data points comprising the Raman spectrum are so determined to be baseline data points consistent with the disclosure below. At block 13, a determination is made regarding others of the Raman spectrum data points so that some of those other Raman spectrum data points are classified as baseline (i.e., noise) data points. A second set of the data points comprising the Raman spectrum are so determined to be baseline data points consistent with the disclosure below. The first and second set of data points are not contiguous, i.e., there are data points on the Raman spectrum between the first and second data points that are peak data points. Therefore, there exists a gap between the first and second set of data points (the gap being due to the peak data points between the first and second set of data points). At block 14, this gap is bridged with a straight line estimation. Therefore, an estimated baseline is obtained which may include the first and second set of data points and the straight line bridging the gap. At block 15, this estimated baseline can be smoothed by applying any one or more smoothing algorithms as known in the art, including a Savitzky-Golay filter. At block 16, the smoothed estimated baseline, sometimes referred to herein as a smoothed baseline, is subtracted from the Raman spectrum thereby resulting in an adjusted-baseline Raman spectrum. The adjusted-baseline Raman spectrum can then be analyzed, for example by an operator or technician, to determine the location, width, height, and other parameters of the Raman signal contained in the Raman spectrum from a sample.

Figure 2:
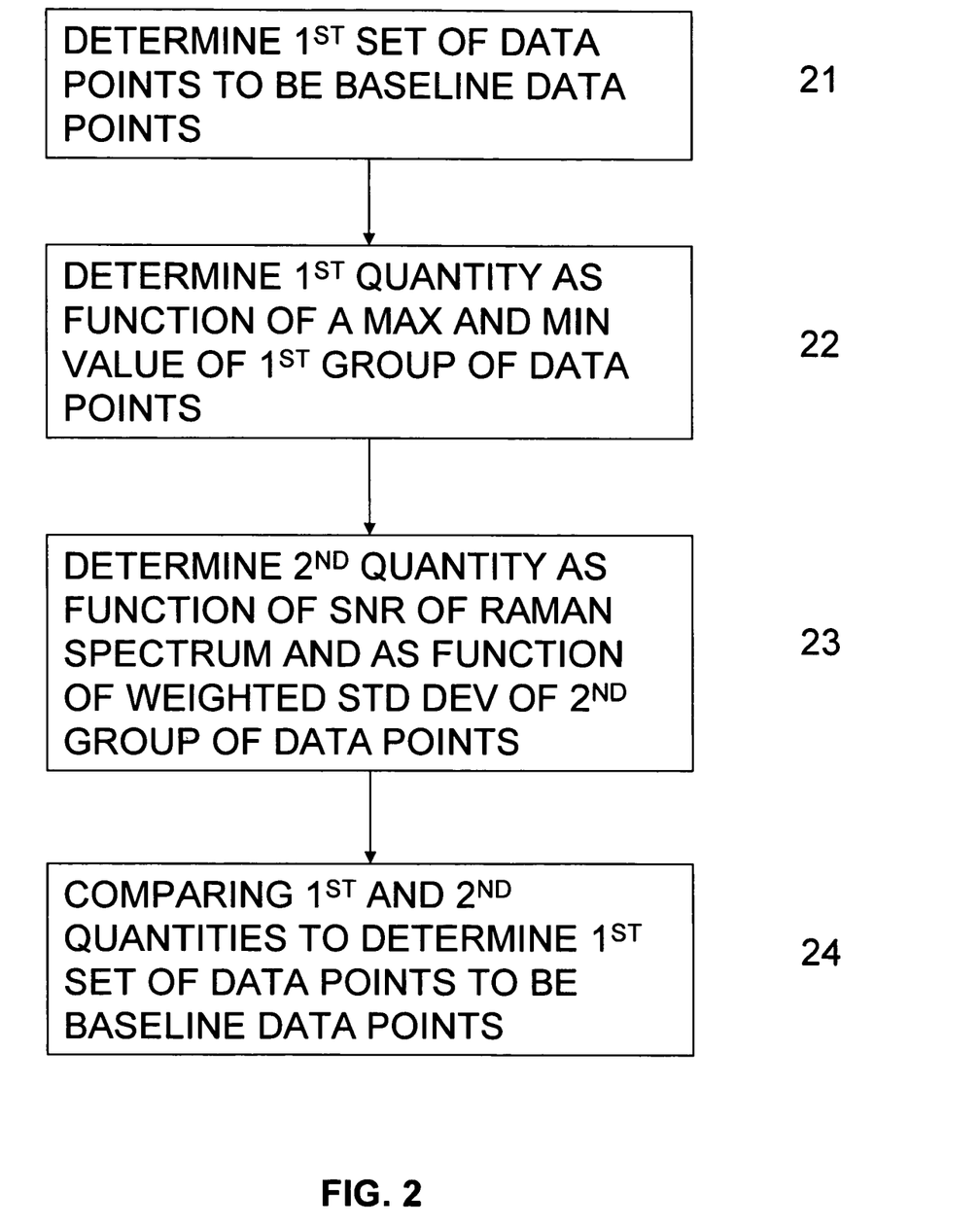
FIG. 2 is a flow chart illustrating procedural steps for determining a set of data points to be baseline data points according to an embodiment of the disclosure.
Figure 6:
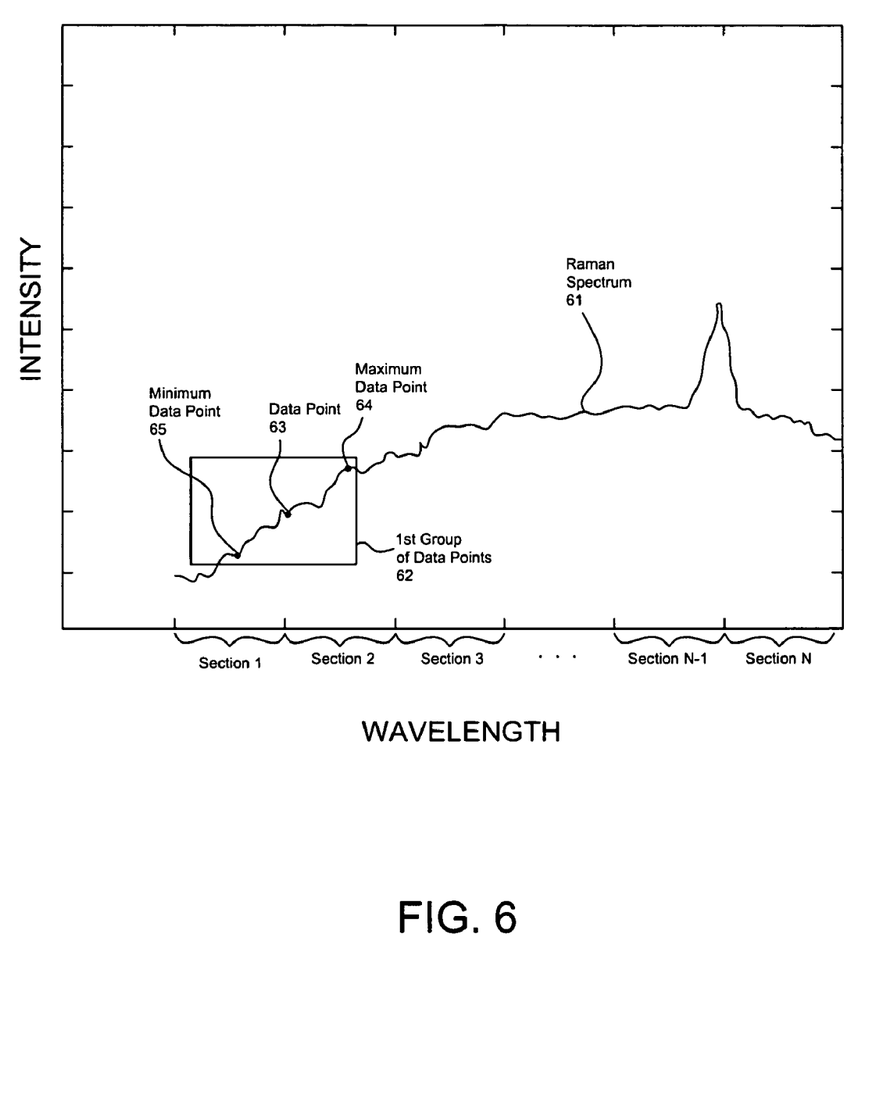
FIG. 6 is a graph showing a Raman spectrum and a first group of data points according to an embodiment of the disclosure.

With attention now directed toward FIG. 2, a flow chart illustrating procedural steps for determining a set of data points to be baseline data points according to an embodiment of the disclosure is shown. FIG. 2 illustrates in more detail block 12 from FIG. 1. As would be obvious to those of skill in the art, FIG. 2 may also be used to illustrate in more detail block 13 from FIG. 1. Block 21 is similar block 12, as discussed above. At block 22, in order to determine if a data point is a baseline data point, an embodiment of the present disclosure determines a first quantity as a function of a maximum value for a first data point and a minimum value for a second data point, where the first and second datapoints are in a first group of data points. As seen in FIG. 6, a Raman spectrum 61 is shown graphed on axes for Intensity ("I") and wavelength ("λ"). As understood by those of skill in the art, the y-axis need not be limited to intensity, but can be any quantity normally used in association with a graph of a Raman spectrum. "Intensity" will be used in the present discussion but should not be construed to limit the invention in any way. A first group of data points 62, which may be referred to herein as a "window of data points" or simply a "window", is illustrated. The window 62 may contain M data points and in one embodiment, M=62. The window 62 contains a data point 63 and may be centered around the data point 63. Within the window 62 are data points of the Raman spectrum 61 including a data point 64 which has a maximum intensity value of the data points within the window 62 and another data point 65 which has a minimum intensity value of the data points within the window 62. The first quantity from block 22 in FIG. 2 is a function of the maximum and minimum data points (in this non-limiting example, data points 64 and 65, respectively) within the window 62, and may be, but is not limited to, a determination according to the following equation:

$$(Y_{max} - Y_{min}) \quad (1)$$

The window 62 may be "slid" along the Raman spectrum so as to calculate a first quantity for select ones, some, most, or all of the data points comprising the Raman spectrum.

With reference again drawn to FIG. 2, at block 23 a second quantity is determined which may be a function of a SNR of the Raman spectrum and/or a function of a weighted standard deviation of data points in a second group of data points. As seen in FIG. 6 along the x-axis (i.e., the wavelength axis), the data points in the Raman spectrum may be divided into N sections. In one embodiment, N=32. In each of these N sections, referred to herein as a second group of data points, a standard deviation of the intensity values of the data points within that particular section is calculated. A weighted average of the standard deviations for each of the N sections is determined and the weighted standard deviation ("$\sigma_{noise}$") value is multiplied by a number n which is a function of a SNR of the Raman spectrum as discussed above. Therefore, the second quantity may be, but is not limited to, a determination according to the following equation:

$$n*\sigma_{noise} \quad (2)$$

Returning again to FIG. 2, at block 24, the first and second quantities are compared and the result of the comparison determines if a particular data point is a baseline (i.e., noise) data point or a signal (i.e., peak) data point. This determination may be, but is not limited to, a determination according to the following equation:

$$(Y_{max} - Y_{min}) < n*\sigma_{noise} \quad (3)$$

In an embodiment of the present disclosure, if the first quantity (i.e., the left hand side of Equation (3)) for a data point is less than the second quantity (i.e., the right hand side of Equation (3)) then the data point is a baseline data point (i.e., noise).

Figure 3:
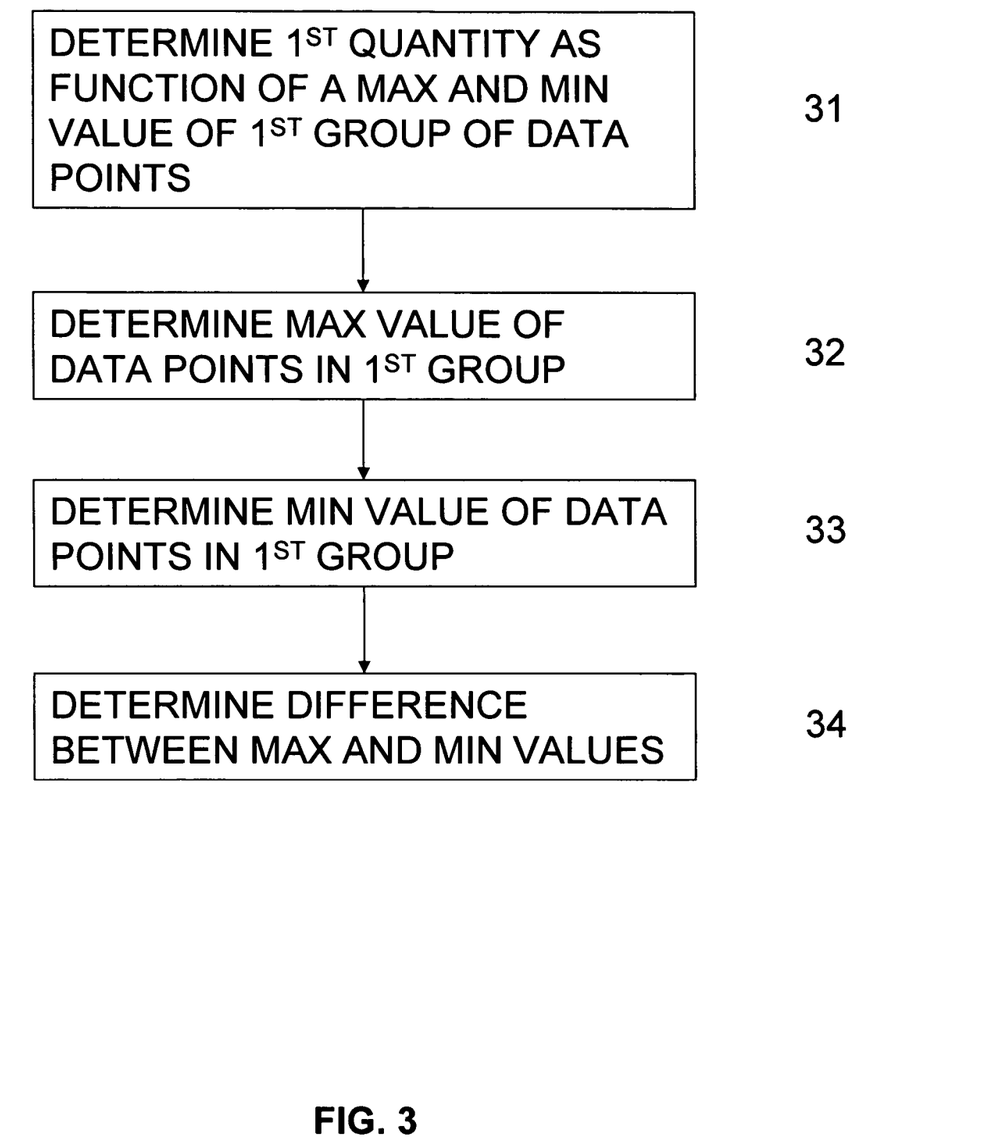
FIG. 3 is a flow chart illustrating procedural steps for determining a first quantity as a function of maximum and minimum values for data points in a first group of data points according to an embodiment of the disclosure.

With reference now to FIG. 3, a flow chart illustrating procedural steps for determining a first quantity as a function of maximum and minimum values for data points in a first group of data points according to an embodiment of the disclosure. FIG. 3 illustrates in more detail block 22 from FIG. 2. Block 31 is similar to block 22, as discussed above. Following the above discussion for Equations (1) and (3), at block 32 a determination of the maximum value of the data points in the first group of data points is made. At block 33, a determination of the minimum value of the data points in the first group of data points is made. At block 34, a difference may be determined between the maximum and minimum value of the data points in the first group of data points, as illustrated above with respect to Equations (1) and (3).

Figure 4:
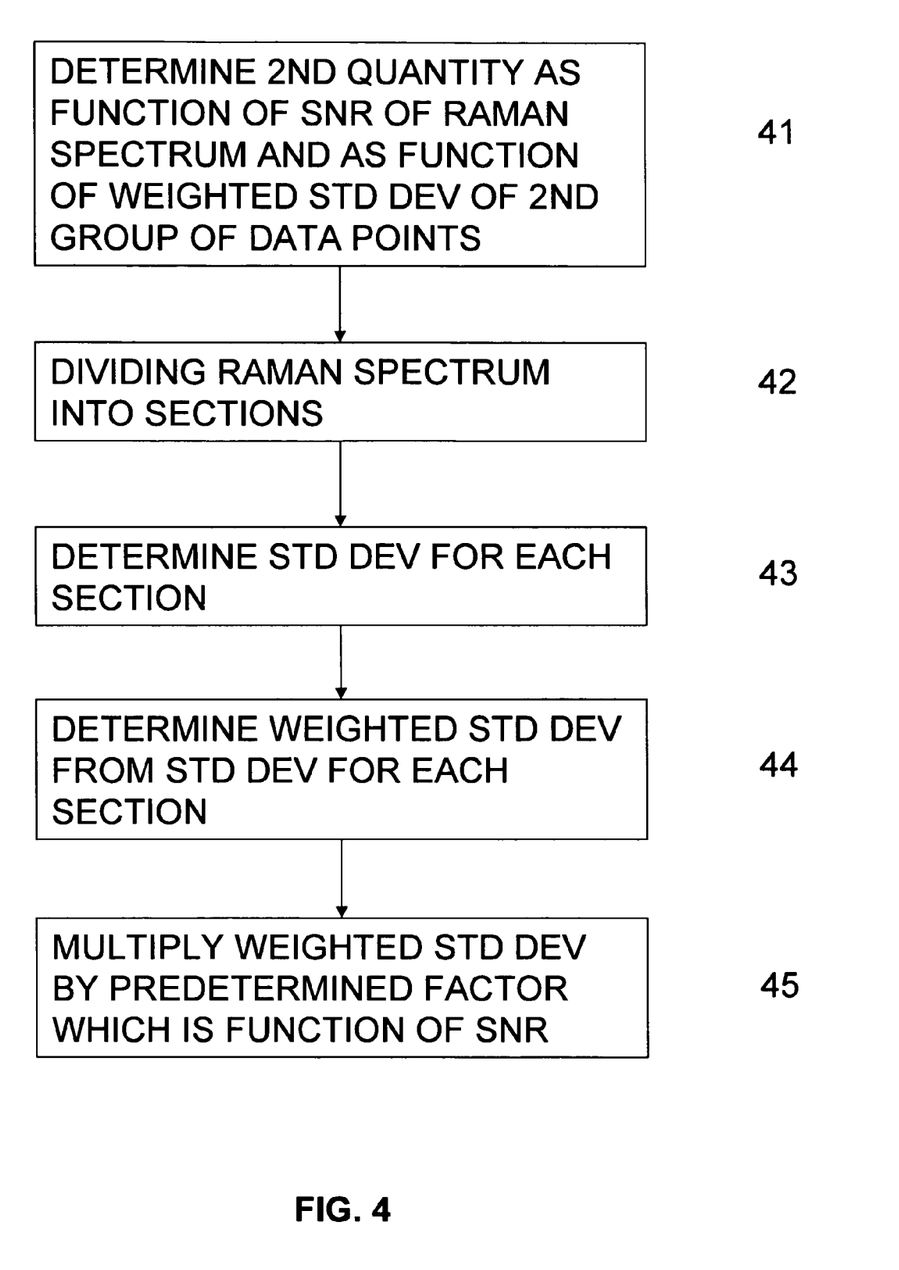
FIG. 4 is a flow chart illustrating procedural steps for determining a second quantity as a function of a signal-to-noise ratio for the Raman spectrum and as a function of a weighted standard deviation of a second group of data points according to an embodiment of the disclosure.
Figure 5:
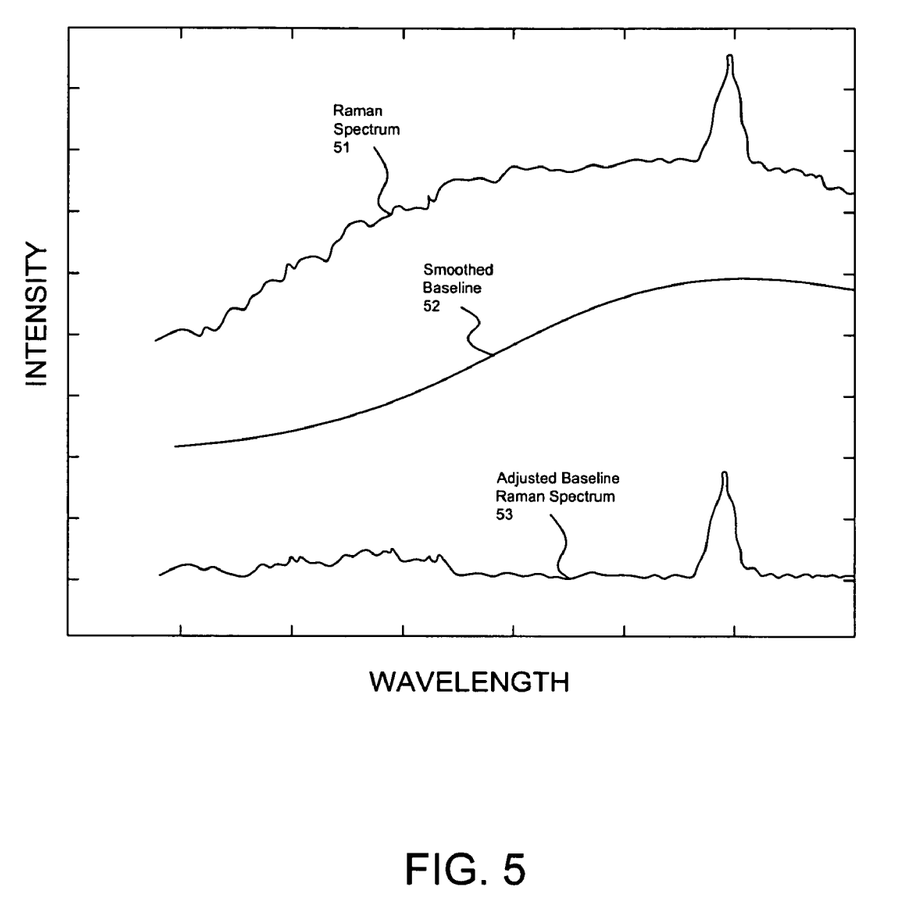
FIG. 5 is a graph showing a Raman spectrum, a smoothed estimated baseline, and an adjusted baseline Raman spectrum according to an embodiment of the disclosure.

With reference now to FIG. 4, is a flow chart illustrating procedural steps for determining a second quantity as a function of a signal-to-noise ratio for the Raman spectrum and as a function of a weighted standard deviation of a second group of data points according to an embodiment of the disclosure. FIG. 4 illustrates in more detail block 23 from FIG. 2. Block 41 is similar to block 23, as discussed above. Following the above discussion for Equations (2) and (3), at Block 42 the Raman spectrum may be divided into N sections. At block 43, a standard deviation for each of the data points in a particular section of data points is determined. At block 44, a weighted standard deviation is determined from the standard deviations for the N sections. At block 45, the weighted standard deviation is multiplied by a factor n which is a function of a SNR of the Raman spectrum, as illustrated above with respect to Equations (2) and (3).

Figure 7:
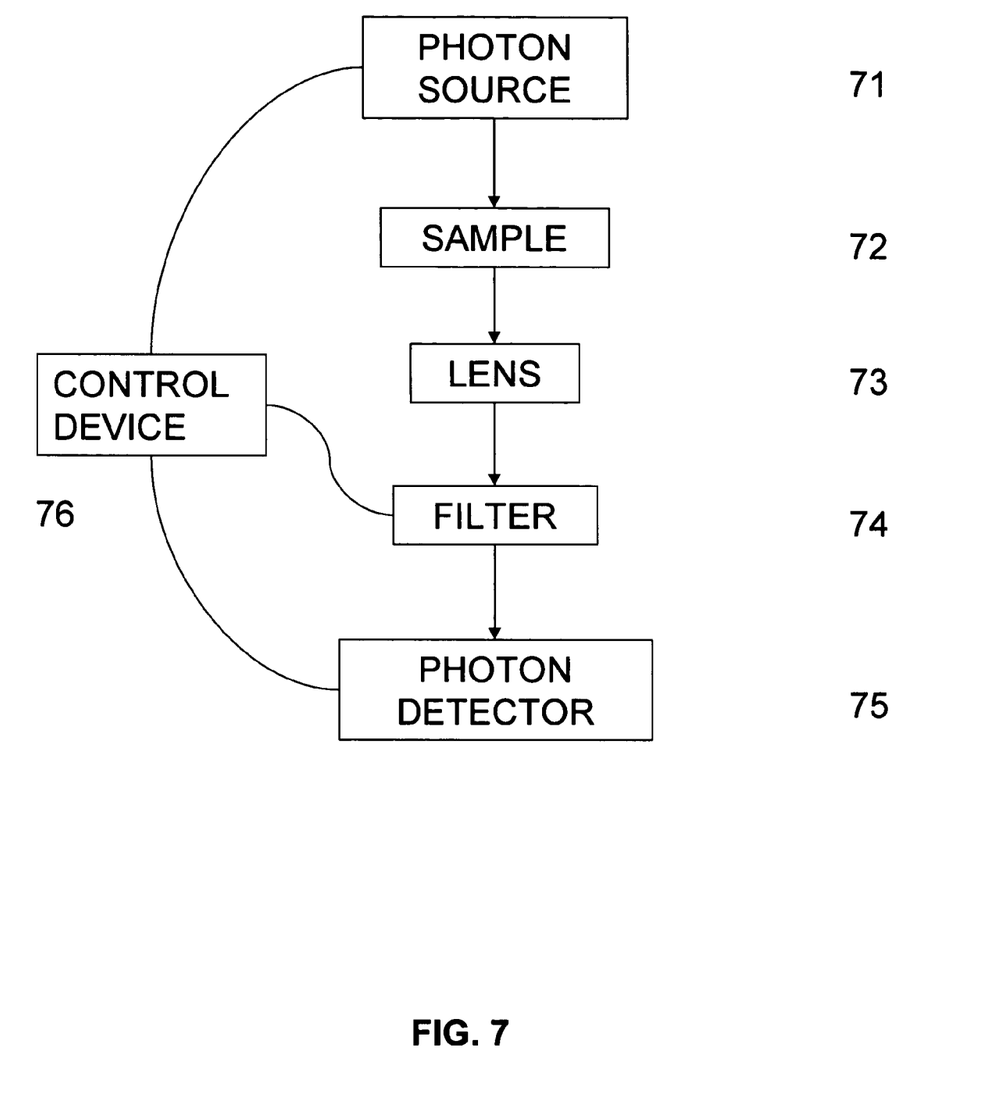
FIG. 7 is a block diagram of an apparatus according to an embodiment of the disclosure.

An apparatus for providing the Raman spectrum is illustrated in FIG. 7 and may include a photon source 71, which may be a laser, which provides illuminating photons to a sample 72. The interaction of the illuminating photons and the sample 72 may create Raman photons which are collected by a lens 73, passed through a filter 74 and detected at a photon detector 75, which may be a Charge-Coupled Device ("CCD"). Additionally, a control device 76 may optionally be operatively connected to the photon source 71, the filter 74 and the photon detector 75. The control device 76 may include: first circuitry for determining the first and second sets of data points to be baseline data points as discussed above; second circuitry for bridging the gap between the first and second sets of data points as discussed above; filtering circuitry, which may be a Savitzky-Golay filter, for smoothing the estimated baseline as discussed above, and signal processing circuitry for determining the adjusted-baseline Raman spectrum as discussed above. Furthermore, the control device may include a display means, such as an electronic display device (as non-limiting examples, a computer screen, a flat panel display, etc.) for displaying the adjusted-baseline Raman spectrum.

In another embodiment, the control device 76 may include a processor programmed to perform a plurality of executable instructions, where the instructions may include: determining the first and second sets of data points to be baseline data points as discussed above; bridging the gap between the first and second sets of data points as discussed above; filtering for smoothing the estimated baseline as discussed above, and signal processing for determining the adjusted-baseline Raman spectrum as discussed above.

The filter 74 may be a Liquid Crystal Tunable Filter ("LCTF"), an Acousto-Optical Tunable Filter ("AOTF"), or a Fiber Array Spectral Translator ("FAST"). The FAST system can provide rapid real-time analysis for quick detection, classification, identification, and visualization of the sample. FAST technology can acquire a few to thousands of full spectral range, spatially resolved spectra simultaneously. This may be done by focusing a spectroscopic image onto a two-dimensional array of optical fibers that are drawn into a one-dimensional distal array with, for example, serpentine ordering. The one-dimensional fiber stack may be coupled to an imaging spectrograph of a CCD, such as the photon detector 75. One advantage of this type of apparatus over other spectroscopic apparatus is speed of analysis. A complete spectroscopic imaging data set can be acquired in the amount of time it takes to generate a single spectrum from a given material. FAST can be implemented with multiple detectors. The FAST system allows for massively parallel acquisition of full-spectral images. A FAST fiber bundle may feed optical information from its two-dimensional non-linear imaging end (which can be in any non-linear configuration, e.g., circular, square, rectangular, etc.) to its one-dimensional linear distal end.

The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

I claim:

1. A method for adjusting a baseline for a Raman spectrum comprising:

(a) providing a Raman spectrum having plural data points wherein each data point has a value associated therewith;

(b) determining a first set of said data points to be baseline data points;

(c) determining a second set of said data points to be baseline data points wherein said second set of data points is not contiguous with said first set of data points;

(d) bridging a gap between said first and second set of data points with a straight line to thereby form an estimated baseline;

(e) smoothing said estimated baseline to thereby form a smoothed baseline; and (f) subtracting said smoothed baseline from said Raman spectrum to thereby provide an adjusted-baseline Raman spectrum, wherein step (b) further comprises (b)(i) determining a first quantity as a function of a maximum and a minimum of the value of the data points in a first group of data points;

(b)(ii) determining a second quantity as a function of a signal to noise ratio of the Raman spectrum and as a function of a weighted standard deviation for the value of the data points in a second group of data points; and (b)(iii) for ones of said data points, comparing the first quantity to the second quantity to thereby determine a first set of data points to be baseline data points.

2. The method of claim 1 wherein step (b)(i) includes:

(b)(i)(A) determining a maximum of the value of the data points in the first group of data points;

(b)(i)(B) determining a minimum of the value of the data points in the first group of data points; and (b)(i)(C) determining a difference between the determined maximum value and the determined minimum value.

3. The method of claim 2 wherein step (b)(ii) includes:

(b)(ii)(A) dividing said Raman spectrum into a predetermined number of sections;

(b)(ii)(B) determining, for each section of said predetermined number of sections, a standard deviation for the value of the data points in said each section;

(b)(ii)(C) determining a weighted standard deviation from said determined standard deviation for each section of said predetermined number of sections; and (b)(ii)(D) multiplying said weighted standard deviation by a predetermined amount wherein said predetermined amount is a function of a signal to noise ratio of the Raman spectrum.

4. The method of claim 3 wherein said predetermined number is 32.

5. The method of claim 3 wherein step (b)(iii) includes determining if the first quantity is less than the second quantity for determining the first set of baseline data points.

6. The method of claim 1 wherein step (e) includes using a Savitzky-Golay filter.

7. The method of claim 1 further comprising the step of displaying the adjusted-baseline Raman spectrum.

8. The method of claim 7 wherein the adjusted-baseline Raman spectrum is displayed on an electronic display device.

9. The method of claim 1 wherein the first and second set of data points are within a predetermined region of said Raman spectrum.

10. The method of claim 9 wherein the predetermined region includes wavenumbers that are between approximately 600 $cm^{-1}$ and approximately 1800 $cm^{-1}$.

11. The method of claim 10 wherein the predetermined region further includes wavenumbers that are greater than approximately 2800 cm$^{-1}$.

12. An apparatus for adjusting a baseline for a Raman spectrum comprising:
    means for providing a Raman spectrum having plural data points wherein each data point has a value associated therewith;
    first circuitry for determining a first set of said data points to be baseline data points and for determining a second set of said data points to be baseline data points wherein said second set of data points is not contiguous with said first set of data points;
    second circuitry for bridging a gap between said first and second set of data points with a straight line to thereby form an estimated baseline;
    filtering circuitry for smoothing said estimated baseline to thereby form a smoothed baseline; and
    signal processing circuitry for subtracting said smoothed baseline from said Raman spectrum to thereby provide an adjusted-baseline Raman spectrum wherein
    said first circuitry determines:
        a first quantity as a function of a maximum and a minimum of the value of the data points in a first group of data points; and
        a second quantity as a function of a signal to noise ratio of the Raman spectrum and as a function of a weighted standard deviation for the value of the data points in a second group of data points; and
    said first circuitry compares, for ones of said data points, the first quantity to the second Quantity to thereby determine a first set of data points to be baseline data points.

13. The apparatus of claim 12 wherein said first circuitry further determines:
    a maximum of the value of the data points in the first group of data points;
    a minimum of the value of the data points in the first group of data points; and
    a difference between the determined maximum value and the determined minimum value.

14. The apparatus of claim 13 wherein said first circuitry:
    divides said Raman spectrum into a predetermined number of sections;
    determines, for each section of said predetermined number of sections, a standard deviation for the value of the data points in said each section;
    determines a weighted standard deviation from said determined standard deviation for each section of said predetermined number of sections; and
    multiplies said weighted standard deviation by a predetermined amount wherein said predetermined amount is a function of a signal to noise ratio of the Raman spectrum.

15. The method of claim 14 wherein said predetermined number is 32.

16. The apparatus of claim 14 wherein said first circuitry calculates if the first quantity is less than the second quantity for determining the first set of baseline data points.

17. The apparatus of claim 12 wherein said filtering circuitry includes a Savitzky-Golay filter.

18. The apparatus of claim 12 further comprising means for displaying the adjusted-baseline Raman spectrum.

19. The apparatus of claim 18 wherein said display means is an electronic display device.

20. The apparatus of claim 12 wherein the first and second set of data points are within a predetermined region of said Raman spectrum.

21. The apparatus of claim 20 wherein the predetermined region includes wavenumbers that are between approximately 600 cm$^{-1}$ and approximately 1800 cm$^{-1}$.

22. The apparatus of claim 21 wherein the predetermined region further includes wavenumbers that are greater than approximately 2800 cm$^{-1}$.

23. The apparatus of claim 21 wherein said means for providing a Raman spectrum includes a fiber array spectral translator.

24. A system for adjusting a baseline for a Raman spectrum comprising:
    means for providing a Raman spectrum having plural data points wherein each data point has a value associated therewith; and
    a processor programmed to perform a plurality of executable instructions, the instructions comprising:
    (a) determining a first set of said data points to be baseline data points, including:
        (i) determining a first quantity as a function of a maximum and a minimum of the value of the data points in a first group of data points;
        (ii) determining a second quantity as a function of a signal to noise ratio of the Raman spectrum and as a function of a weighted standard deviation for the value of the data points in a second group of data points; and
        (iii) for ones of said data points, comparing the first quantity to the second quantity to thereby determine a first set of data points to be baseline data points;
    (b) determining a second set of said data points to be baseline data points wherein said second set of data points is not contiguous with said first set of data points, including:
        (i) determining a third quantity as a function of a maximum and a minimum of the value of the data points in a third group of data points;
        (ii) determining a fourth quantity as a function of a signal to noise ratio of the Raman spectrum and as a function of a weighted standard deviation for the value of the data points in a fourth group of data points; and
        (iii) for other ones of said data points, comparing the third quantity to the fourth quantity to thereby determine a second set of data points to be baseline data points;
    (c) bridging a gap between said first and second set of data points with a straight line to thereby form an estimated baseline;
    (d) smoothing said estimated baseline to thereby form a smoothed baseline; and
    (e) subtracting said smoothed baseline from said Raman spectrum to thereby provide an adjusted-baseline Raman spectrum.

25. The system of claim 24 wherein for (a)(i) said processor is further programmed to execute the instructions of:
    determining a maximum of the value of the data points in the first group of data points;
    determining a minimum of the value of the data points in the first group of data points; and
    determining a difference between the determined maximum value and the determined minimum value.

26. The system of claim 25 wherein for (a)(ii) said processor is further programmed to execute the instructions of:

dividing said Raman spectrum into a predetermined number of sections;

determining, for each section of said predetermined number of sections, a standard deviation for the value of the data points in said each section;

determining a weighted standard deviation from said determined standard deviation for each section of said predetermined number of sections; and multiplying said weighted standard deviation by a predetermined amount wherein said predetermined amount is a function of a signal to noise ratio of the Raman spectrum.

27. The system of claim 26 wherein for (a)(iii) said processor is further programmed to execute the instruction of determining if the first quantity is less than the second quantity for determining the first set of baseline data points.

28. A method for adjusting a baseline for a Raman spectrum comprising:

(a) providing a Raman spectrum having plural data points wherein each data point has a value associated therewith;

(b) selecting a computational window having a width of a maximum of M number of data points;

(c) computationally placing said window over each data point of said plural data points to thereby determine a corresponding first quantity for each said data point;

(d) dividing said Raman spectrum into a predetermined number of sections, wherein each section includes a portion of said plural data points;

(e) determining a second quantity as a function of a signal to noise ratio of the Raman spectrum and as a function of a weighted standard deviation of the values of the data points in all of said predetermined number of sections;

(f) for each of said plural data points, comparing the corresponding first quantity to the second quantity to thereby determine whether said data point is a baseline data point or a non-baseline data point;

(g) connecting all data points determined to be baseline data points and bridging a gap between any two baseline data points separated by one or more non-baseline data points with a straight line to thereby form an estimated baseline;

(h) smoothing said estimated baseline to thereby form a smoothed baseline; and (i) subtracting said smoothed baseline from said Raman spectrum to thereby provide a baseline-adjusted Raman spectrum.

29. The method of claim 28 wherein a value of M is user-selected.

30. The method of claim 28 wherein M=62.

31. The method of claim 28 wherein step (c) further comprises:

(c)(i) treating a data point from said plural data points as a focus data point of said window, wherein up to N−1 data points neighboring said focus data point in said Raman spectrum are treated as part of said window;

(c)(ii) for said focus data point, determining said corresponding first quantity as a function of a maximum and a minimum of the values of all the data points in said window; and (c)(iii) iteratively repeating steps (c)(i) and (c)(ii) for each of said plural data points in said Raman spectrum, thereby determining said corresponding first quantity for each of said plural data points.

* * * * *